United States Patent [19]

Ong

[11] 4,365,360
[45] Dec. 28, 1982

[54] LENS DESIGNED FOR IMPLANTATION INTO A LENS CAPSULE OF A HUMAN EYE

[76] Inventor: Tiong S. Ong, 174 Ghijseland, 3161 Vm Rhoon, Netherlands

[21] Appl. No.: 329,811

[22] Filed: Dec. 11, 1981

Related U.S. Application Data

[63] Continuation of Ser. No. 134,892, Mar. 28, 1980, abandoned.

[30] Foreign Application Priority Data

Apr. 5, 1979 [NL] Netherlands ............... 7902703

[51] Int. Cl.³ ..................... A61F 1/16; A61F 1/24
[52] U.S. Cl. ............................................. 3/13
[58] Field of Search ................................. 3/13

[56] References Cited

U.S. PATENT DOCUMENTS

| | | | |
|---|---|---|---|
| 2,834,023 | 5/1958 | Lieb | 3/13 X |
| 3,994,027 | 11/1976 | Jensen et al. | 3/13 |
| 4,110,848 | 9/1978 | Jensen | 3/13 |
| 4,251,887 | 2/1981 | Anis | 3/13 |

FOREIGN PATENT DOCUMENTS

| | | | |
|---|---|---|---|
| 2717706 | 10/1978 | Fed. Rep. of Germany | 3/13 |
| 563174 | 7/1977 | U.S.S.R. | 3/13 |

*Primary Examiner*—Ronald L. Frinks
*Attorney, Agent, or Firm*—Silverman, Cass & Singer, Ltd.

[57] ABSTRACT

The present invention is a lens designed for implantation into the capsule of a human eye. The element forming the optic component is provided with supporting loops, the ends of which have been inserted into the periphery of said element, through holes being provided in said periphery. The loops are securely anchored in two capsular pockets after affected portions of the natural lens and a front part of the capsule, have been removed.

5 Claims, 7 Drawing Figures

LENS DESIGNED FOR IMPLANTATION INTO A LENS CAPSULE OF A HUMAN EYE

This is a continuation, of application Ser. No. 134,892 filed Mar. 28, 1980, now abandoned.

BACKGROUND OF THE INVENTION

1. Field of the Invention

The present invention relates to a lens designed for implantation into a lens capsule of a human eye, which may be surgically implanted and to a method of performing said implantation.

2. Description of the Prior Art

In the prior art lenses have been used in an operation for surgically implanting a lens in the anterior eye chamber after having evacuated impure aqueous humor. The flat back side of a planoconvex lens made e.g. from polymethylene methacrylate is positioned directly before the iris of the eye whilst from the back side of the lens, supporting loops extend outwardly in a radial direction from the lens and get engaged behind the iris. Efforts have also been made to implant a lens into the posterior chamber of the human eye, but these have not been successful up till now as the manner in which these lenses were secured either damages the cornea or also deformed the pupil since the edges of the iris came to lie in between the implanted element and the loops.

West German Offenlegungsschrift No. 2,717,706 entitled: "Lens for implanting into the lens capsule of the eye", in the name of Leonhard Klein, issued on Oct. 26, 1978, teaches a lens for implantation in the lens capsule of the eye, the periphery of the lens comprising two or a plurality of soft and elastic supports in the form of rings being positioned remote from the inner circumference of the capsule. In this type of lens the support rings functioning as centering rings have to be implanted alternately whilst the implantation proper of the lens takes place by means of sucking with an elastic precision sucker. The difficulty with this type of lens is that an alternate positioning of the support rings and an implantation and securing of the lens by means of sucking may damage the eye capsule and the tissues thereof, whilst furthermore a rigid anchoring of the implanted lens which is secured by means of sucking, is not entirely ensured, whereas a plurality of support rings cannot be inserted through the opening made in the capsule. It would be far better to use two diametrical supporting loops facing each other instead of rings, said loops being inserted into an element forming the optic component and to obtain capsular pockets into which the supporting loops are anchored, the element being implanted in the remaining portion of the capsule.

U.S. Pat. No. 4,056,855 entitled "Intraocular lens and method of implanting same", issued on Nov. 8, 1977 to Kelman, describes an intraocular lens and a method of its implantation through an incision in the eye. The assembly includes a lens member and a supporting wire initially in disassembled condition and adapted to be introduced independently through a small incision in the eye. The supporting wire has a base portion, which is adapted to fit and be mounted behind the iris of the eye and has a pair of resilient legs projecting from the pupil, forward of the iris, said legs being adapted to receive a lens therebetween, snapped into position by resiliently parting the legs while both components are located in the eye and thereby assembling and mounting the intraocular lens in position in the anterior chamber of the eye. The difficulty with this type of lens is that in first instance it is not integral so that a shifting or turning of the assembly may nevertheless take place, while a position in the anterior eye chamber is unnatural and may create a problem in the restoration of accurate binocular vision. Further the lens in the anterior chamber is not adjacent to the hyloid membrane for supporting the vitreous humor whilst the pupil further looses its original round shape which may also form an objection to accurate vision.

U.S. Pat. No. 4,071,343 entitled: "Method of making intraocular lenses", issued to Walter P. Sigmund teaches the production of optical sections (lenses) of pseudophakoi, having tangential holes without drilling operations. Said lens is adapted to be positioned in holes in a lens. The difficulty with this product is that it does not form an initial assembly so that a continuous anchoring of same is not ensured whilst rods or prongs have to be fixed in the lens proper which may damage said lens while moreover a shifting or turning over of the relative product could cause an inflammation and thus an erosion of the iris so that the binocular vision could be hampered. Moreover the pupil will loose its original round shape.

U.S. Pat. No. 4,110,848, entitled: "Intraocular lens for implantation into the posterior chamber of a human eye", issued to Ronald P. Jensen on Sept. 5, 1978, teaches an intraocular lens for implantation into the posterior chamber of a human eye including a plano-convex lens, adapted to be inserted into the posterior chamber of the eye within the capsular membrane thereof. The lens includes two supporting loops being mechanically coupled to the peripheral edge of said lens and being disposed at an angle in the range of 0° to 25° to the plane surface of the plano-convex lens. The end portions of the supporting loops are below the plane surface of said lens. One supporting loop is so designed that it comprises a notch which is disposed between the peripheral edge of the plano-convex lens and its end portions so that a temporarily securement to the iris of the human eye may be accomplished. The difficulty with a lens of this type is that it is anchored in the capsular membrane formed by the anterior and posterior membranes gathering together. It would be far better to have the supporting loops anchored in capsular pockets formed by leaving a portion of anterior membrane, so that a rigid anchoring is ensured. The lens as described further provides one supporting loop which includes a notch, said supporting loop being disposed between the peripheral edge of the plano-convex lens, only ensuring a temporarily securement to the iris of the eye until a capsular fixation occurs, a position which might be dangerous since in this case the said securement could be hampered, thus involving s shifting or turning over of the respective lens and an inflammation of the iris.

SUMMARY OF THE INVENTION

In view of the foregoing factors and conditions of the prior art it is a primary object of the present invention to provide a lens which is to be positioned in the posterior chamber of the human eye and which is anchored securely in the capsular pockets, formed by perforating the capsule and evacuation of the affected lens portion.

It is another object of the present invention to provide a lens which comprises two diametrical supporting loops facing one another, one loop of which extends circularly and toward a radial direction of the lens element, the deflection of said loop exceeding that of the second supporting loop.

It is still another object of the invention to provide a lens which does not deform the original round shape of the natural lens and which allows for an increased binocular power.

It is yet another object of the present invention to provide a lens for implantation into the posterior chamber of the human eye and which comprises at least two apertures being positioned in the peripheral area of the lens and which apertures allow for a firm grip upon the lens to be implanted, if desired by means of a precision tweezer or a fork adapted for this purpose.

It is yet still another object of the present invention to provide a lens for implantation into the capsule of a human eye, the lens being implanted in the remaining portion of the lens capsule, by means of supporting loops being positioned in the capsular pockets, the latter ensuring a secure anchoring of said lens.

In accordance with an embodiment of the present invention a lens for implantation into the capsule of a human eye is described. The lens includes two diametrically positioned supporting loops facing one another, which are formed from a material that is suitable for an implantation into an eye. One supporting loop extends circularly and radially from the element forming the optic component and has a deflection exceeding that of the other supporting loop. Two peripheral apertures allow for a good grip to be obtained upon the lens to be implanted by means of a precision tweezer or a fork adapted for that purpose, by means of which the lens can be handled.

In a preferred embodiment of the present invention the back side of the optic component forming the lens is entirely smooth, so that said back side may intimately adjoin the lens capsule, whilst the periphery of the component comprises holes for inserting the ends of the two opposite supporting loops.

The features of the present invention which are believed to be novel are set forth with particularity in the appended claims.

Other claims and many of the attendant advantages will be more readily appreciated as the same becomes better understood by reference to the following detailed description and considered in connection with the accompanying drawings in which like reference symbols designate like parts throughout the figures.

DESCRIPTION OF A PREFERRED EMBODIMENT

Figure 1:
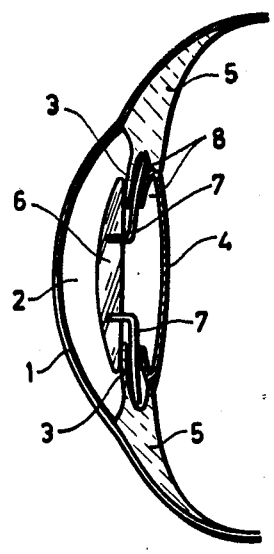
FIG. 1 is a vertical cross-section of the front part of a human eye wherefrom the original lens has been removed and replaced by a lens in the anterior eye chamber.
Figure 2:
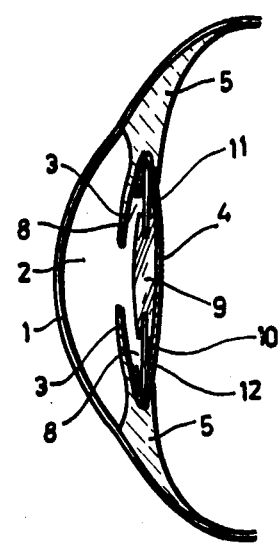
FIG. 2 is a cross-section corresponding to FIG. 1 but presently illustrating a lens according to the invention, being implanted into the posterior eye chamber.

In order to best understand the present invention a description of a preferred embodiment thereof is provided accompanied by drawings. Referring to FIGS. 1 and 2 the cornea is referenced 1 and the anterior eye chamber 2 is positioned behind said cornea and in front of the iris 3. The lens capsule, the back side 4 of which is shown, is supported by tissues 5. The anterior eye chamber 2 comprises a lens, consisting of an element 6, forming the optic component and including two loops 7. The element 6 is a plano-convex lens and replaces the original natural lens which has been removed from the capsule 4. The circumference of the element 6 is positioned in front of the iris 3, whilst the loops 7 extend outwardly from the flat back side of the element 6, and are positioned behind the iris 3, in view of their being radially curved toward the outside. As the manner in which a lens of this type is implanted does not form part of the subject matter of the present invention, this will not be elucidated hereafter. It is, however, obvious that in this case the action of the iris is hampered when the pupil is narrowed, this contrary to the implantation of a lens in the posterior eye chamber 8 according to the present invention.

FIG. 2 clearly shows that, notwithstanding any action of the iris, the round shape of the pupil is entirely maintained. In order to enable the latter, the lens in accordance with the invention is so designed that the element 9 forming the optic component comprises loops 11 and 12 extending beyond the periphery 10 of the element, either end of said loops being attached to said element 9 via said periphery 10.

To that end the back side of the element 9 is entirely smooth and may therefore adjoin the rear part 4 of the lens capsule, without any problems occurring.

Figure 3:
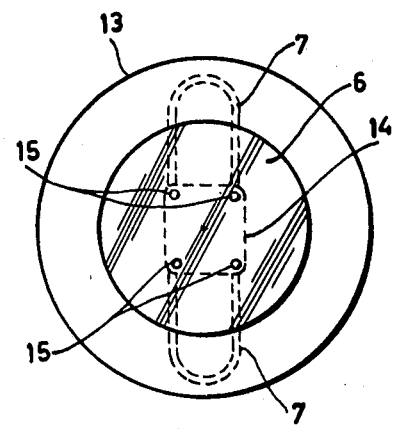
FIG. 3 is a schematic front view of a lens implanted according to FIG. 1.

Preferring now to FIG. 3 a front view of the lens of FIG. 1 is shown with an element 6 which is accommodated in the anterior eye chamber, the circumference of which is indicated by a line 13. A broken line 14 shows the inner edge of iris 3, forming the pupil. It is obvious from said broken line 14 that said pupil is deformed by the loops 7 which hamper a narrowing of said pupil, to wit in particular the parts 15 of the loops 7 being inserted into the back side of the element 6. The pupil may hereby get a square shape and is being irritated. The iris may even get torn.

Figure 4:
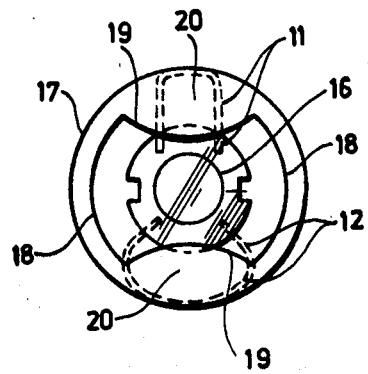
FIG. 4 is a schematic front view of a lens implanted according to FIG. 2.

On comparing the latter with FIG. 4, it will be obvious that the pupil of a lens being implanted in the posterior eye chamber, may maintain its normal round shape, as indicated by line 16.

Line 17 in FIG. 4 shows the periphery of the eye capsule, the front side of which will be removed by means of a row of perforations, as illustrated by arched lines 18, showing the outer discissions, in between which discissions, lobed discissions are applied according to lines 19. From this it follows that the lines 19 are disposed biconcave with respect to one another. This causes two capsular pockets 20 to be obtained in which the supporting loops 11 and 12 may come to lie.

Figures 5, 6:
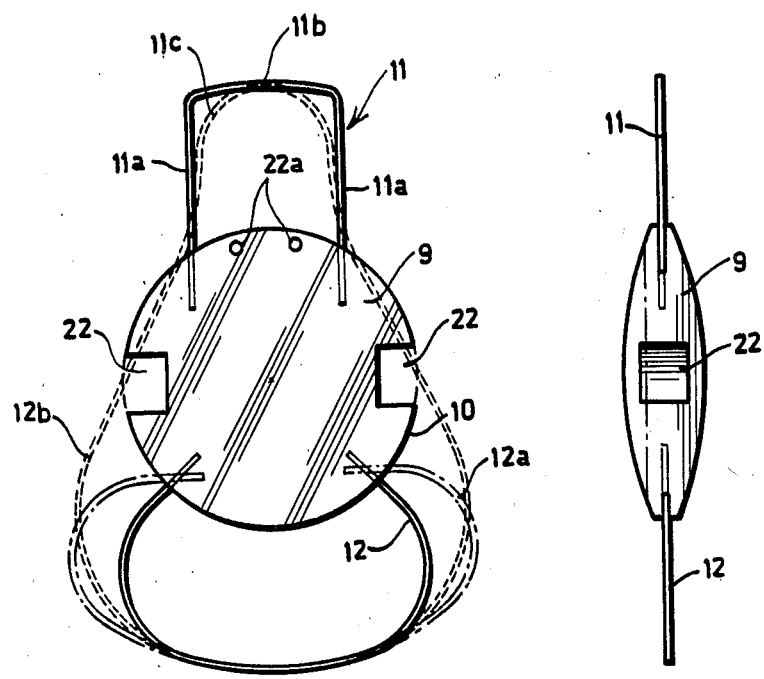
FIG. 5 is a front view of a lens in accordance with the invention.
FIG. 6 is an elevational view of the lens as shown in FIG. 5.

FIG. 5 shows an enlarged front view of the lens according to the invention as shown in FIG. 2 and FIG. 6 shows an enlarged lateral view of the lens according to the present invention as shown in FIG. 4. Element 9 hereby comprises two supporting loops being positioned diametrically with respect to one another, loop 12 extending in a curved ovaloid manner thus causing same to be resiliently deformable and easily radially deflected. So as to improve said deflection the loop may also extend in a manner as illustrated by the dash-dotted line 12a. Loop 11 extends rectangularly as a U-shaped configuration and comprises a slightly curved central part 11b between its legs 11a, the radius of curvature of said part 11b approximately corresponding with line 17, which illustrates the periphery of the lens capsule or of the posterior eye chamber. The supporting loop 11 is subsequently rather rigid toward a radial direction and hence, relatively radially inwardly non-deformable, thus causing the lens to be implanted, to be handled easily by means of a tweezer 21 or a fork (vide FIG. 7). An important connection of the loops can be obtained if the loops are formed as indicated by the dash-dotted line 12b. In this case part 11c of loop 11 has a lesser curvature because of loop 12a having a wider configuration. The extreme ends of the loops 11 and 12 are inserted into the periphery of the element 9, so that not only the front side of said element 9 is smooth but the back side as well. Said back side has a convex shape, which results in the element 9 forming a bi-convex lens, as can be clearly seen in FIG. 6. Said bi-convex shape presents the additional advantage that the back side of the element 9 intimately adjoins the lens capsule 4. Should a capsule discission of the latter portion be essential, the respective aperture applied herein will stay sealed off, in view of which aqueous humor of which the vitreous body consists, cannot possibly penetrate into the posterior and anterior eye chamber. The bi-convex shape of the lens to be implanted also allows an increased lens power to be used.

Figure 7:
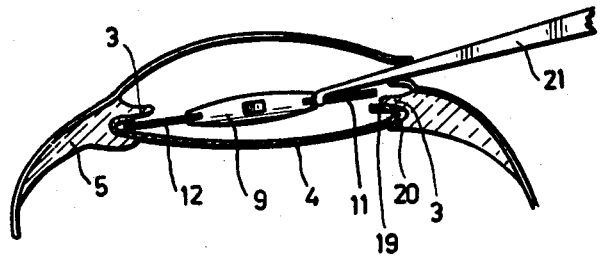
FIG. 7 is a cross-section through an eye showing in which manner a lens according to FIG. 5 has been implanted into the posterior eye chamber.

Notwithstanding the above-described, a plano-convex lens may also be used, the smooth portion of which is then positioned at the front side. Said smooth portion is illustrated in FIG. 6 by a partially dotted line. The implantation of a lens in the posterior eye chamber requires a lens power exceeding that of a lens implanted in the anterior eye chamber. A power being increased as yet, may be obtained by giving the front side a concave shape. Together with the aqueous humor in the anterior eye chamber a composite lens is then obtained. On implanting the lens in the posterior eye chamber, as is shown in FIG. 7, the loop 12 may be slightly pressed into the tissue 5, thus causing same to press the outer edge of the loop 11, the iris, and the lobe 19, so that said loop 12 can be positioned in a capsular pocket 20, formed by lobe 19. It will be obvious that during said operation the pupil is temporarily enlarged. It is furthermore essential to have the implanted lens accurately positioned, so causing the loops 11 and 12 to come to lie in the capsular pockets 20 in a correct and precise manner. The periphery 10 of the element 9 to that end comprises apertures 22 as shown in FIG. 5, so allowing the lens to be slightly turned by means of a tweezer or fork. Said FIG. 5 shows two peripheral apertures 22, being positioned diametrically with respect to the element 9 so that each peripheral aperture is positioned between two loops. Use can be made of two apertures 22a into which a fork (not shown) can be inserted for handling the lens. In such a case the apertures 22 can be omitted.

A method for implantation of a lens into the capsule of a human eye is performed as follows:

A front portion of the lens capsule 4 is removed according to lines 18 and 19 in the drawings, after having perforated said portion. Two diametric capsular pockets 20 are maintained along the border edges of the capsule, due to the presence of lobed discissions 19 which form bi-concave parts whereby the lens element comprising the supporting loops 11 and 12 is implanted in the remaining portion of the lens capsule and is positioned in the capsular pockets 20, so obtained. The peripheral apertures 22 moreover provide a good access toward the space behind the implanted lens in the posterior eye chamber, for example when irrigations have to be performed by means of suitable tubes or when capsular discissions have to be made.

What is claimed is:

1. An intraocular lens implantable into the posterior chamber of a human eye without fixating sutures, comprising an optical lens body and at least a pair of loop shaped members fixed to the periphery of said lens body and extending outwardly from generally opposed sides thereof, one member being of U-shaped configuration and the other member being ovaloid, said ovaloid member being relatively radially inwardly resiliently deformable and said U-shaped member being relatively radially inwardly non-deformable.

2. An intraocular lens according to claim 1, wherein said lens body has hole pairs formed therein for housing the ends of legs of said loop shaped members, one of said hole pairs being parallel for housing the legs of said U-shaped loop, the holes of the other pair converging inwardly for housing the ends of the legs of said ovaloid member.

3. An intraocular lens according to claim 1, wherein the said lens body has hole pairs formed therein for housing the ends of legs of said members, the distance, at the periphery of said lens body, between two holes forming the members of one pair for housing the leg ends of said U-shaped loop being relatively close together, at the periphery of said lens body, and the distance, at the periphery of said lens body between two holes forming the other pair for housing the leg ends of the ovaloid member being relatively far apart.

4. A method for the implantation without fixating sutures of an intraocular lens as set forth in claim 1 in the natural lens capsule of a human eye comprising the steps of perforating the anterior membrane of said natural lens capsule to provide a plurality of perforations defining a predetermined pattern, removing the affected natural lens leaving two lobes with a portion of the anterior membrane surrounded by the perforations, implanting the intraocular lens in the remaining part of said lens capsule and disposing the loops of said lens behind said lobes.

5. A method for implantation without fixating sutures of an intraocular lens in the lens capsule of a human eye, comprising the steps of (a) perforating the anterior membrane of the natural lens capsule to provide a plurality of perforations defining a predetermined pattern;

(b) removing both the affected natural lens portions and a portion of the natural lens capsule surrounding the perforations leaving a remainent portion having two lobes;

(c) providing an intraocular lens having an optical body and at least a pair of loop shaped members fixed to the periphery of said body and extending outwardly from opposed sides, one loop member being of U-shaped configuration and the other member being ovaloid with said ovaloid member being relatively inwardly resiliently deformable and said U-shaped member being relatively radially inwardly non-deformable;

(d) implanting the intraocular lens in the remainent portion of the natural lens capsule; and (e) inserting the loop members behind said lobes of the remainent portion of the natural lens capsule.

* * * * *